US009977036B2

(12) United States Patent
Schutzer

(10) Patent No.: US 9,977,036 B2
(45) Date of Patent: May 22, 2018

(54) DIAGNOSTIC MARKERS FOR MULTIPLE SCLEROSIS

(71) Applicant: Steven E. Schutzer, Water Mill, NY (US)

(72) Inventor: Steven E. Schutzer, Water Mill, NY (US)

(73) Assignee: Steven E. Schutzer, New York, NY (US)

( * ) Notice: Subject to any disclaimer, the term of this patent is extended or adjusted under 35 U.S.C. 154(b) by 0 days. days.

(21) Appl. No.: 14/911,289

(22) PCT Filed: Aug. 15, 2014

(86) PCT No.: PCT/US2014/051215
§ 371 (c)(1),
(2) Date: Feb. 10, 2016

(87) PCT Pub. No.: WO2015/023920
PCT Pub. Date: Feb. 19, 2015

(65) Prior Publication Data
US 2016/0187354 A1    Jun. 30, 2016

Related U.S. Application Data

(60) Provisional application No. 61/866,319, filed on Aug. 15, 2013.

(51) Int. Cl.
| | |
|---|---|
| A61K 38/21 | (2006.01) |
| G01N 33/68 | (2006.01) |
| C12Q 1/68 | (2018.01) |
| A61K 31/136 | (2006.01) |
| A61K 31/137 | (2006.01) |
| A61K 31/225 | (2006.01) |
| A61K 31/277 | (2006.01) |
| A61K 38/02 | (2006.01) |
| C07K 16/28 | (2006.01) |

(52) U.S. Cl.
CPC ....... *G01N 33/6896* (2013.01); *A61K 31/136* (2013.01); *A61K 31/137* (2013.01); *A61K 31/225* (2013.01); *A61K 31/277* (2013.01); *A61K 38/02* (2013.01); *A61K 38/215* (2013.01); *C07K 16/2839* (2013.01); *C12Q 1/6883* (2013.01); *C07K 2317/24* (2013.01); *C07K 2317/76* (2013.01); *C12Q 2600/158* (2013.01); *G01N 2333/47* (2013.01); *G01N 2333/485* (2013.01); *G01N 2333/705* (2013.01); *G01N 2800/285* (2013.01)

(58) Field of Classification Search
None
See application file for complete search history.

(56) References Cited

U.S. PATENT DOCUMENTS

| 8,394,583 B2 | 3/2013 | Monson |
| 2004/0018522 A1 | 1/2004 | Dangond et al. |
| 2008/0274456 A1 | 11/2008 | Yankner et al. |
| 2009/0124542 A1 | 5/2009 | Hageman et al. |
| 2012/0252874 A1 | 10/2012 | Feinstein et al. |

FOREIGN PATENT DOCUMENTS

| WO | 2010034514 | 4/2010 |
| WO | 2011142827 | 11/2011 |

OTHER PUBLICATIONS

Satoh et al., Nogo-A and Nogo Receptor Expression in Demyelinating Lesions of Multiple Sclerosis, Feb. 2005, Neuropathol Exp Neurol 64(2):129-138.*
Muramatsu et al., RGMa modulates T cell responses and is involved in autoimmune encephalomyelitis, Apr. 2011, Nature Medicine 17(4):488-495.*
Di Rosa et al., "Evaluation of CHI3L-1 and CHIT-1 expression in differentiated and polarized macrophages", Inflammation, 2013, 36:482-92.
Agrawal S et al (2006) Dystroglycan is selectively cleaved at the parenchymal basement membrane at sites of leukocyte extravasation in experimental autoimmune encephalomyelitis. J Exp Med 203(4):1007-1019.
Calabrese M et al (2011) The predictive value of gray matter atrophy in clinically isolated syndromes. Neurology 77(3): 257-263.
Comabella M et al (2010) Cerebrospinal fluid chitinase 3-like 1 levels are associated with conversion to multiple sclerosis. Brain 133:1082-1093.
del Zoppo GJ et al (2006) Integrin-matrix interactions in the cerebral microvasculature. Arterioscler Thromb Vasc Biol 26(9):1966-1975.
Derfuss T et al (2009) Contactin-2/TAG-1-directed autoimmunity is identified in multiple sclerosis patients and mediates gray matter pathology in animals. Proc Natl Acad Sci USA 106(20): 8302-8307.
Dhaunchak AS et al (2012) Implication of perturbed axoglial apparatus in early pediatric multiple sclerosis. Ann Neurol 71(5): 601-613.
Dotevall et al (1999) Astroglial and neuronal proteins in cerebrospinal fluid as markers of CNS involvement in Lyme neuroborreliosis. Eur J Neurol 6(2):169-178.
Freedman MS et al (2005) Recommended standard of cerebrospinal fluid analysis in the diagnosis of multiple sclerosis: a consensus statement. Arch Neurol 62(6):865-870.
Fu QL et al (2011) Soluble Nogo-66 receptor prevents synaptic dysfunction and rescues retinal ganglion cell loss in chronic glaucoma. Invest Ophthalmol Vis Sci 52(11):8374-8380.
Jurewicz A et al (2007) Soluble Nogo-A, an inhibitor of axonal regeneration, as a biomarker for multiple sclerosis. Neurology 68(4):283-287.
Kroksveen AC et al (2013) Discovery and initial verification of differentially abundant proteins between multiple sclerosis patients and controls using iTRAQ and SID-SRM. J Proteomics 78:312-325.
Lee H et al (2008) Synaptic function for the Nogo-66 receptor NgR1: regulation of dendritic spine morphology and activity-dependent synaptic strength. J Neurosci 28(11): 2753-2765.
Massaro AR et al (2009) The neural cell adhesion molecule (NCAM) present in the cerebrospinal fluid of multiple sclerosis patients is unsialylated. Eur Rev Med Pharmacol Sci 13(5):397-399.

(Continued)

*Primary Examiner* — John D Ulm
(74) *Attorney, Agent, or Firm* — Klauber & Jackson LLC

(57) ABSTRACT

Biomarkers and uses thereof, as well as methods for using same for diagnosing first-attack multiple sclerosis are described herein.

16 Claims, 6 Drawing Sheets

(56) References Cited

OTHER PUBLICATIONS

McDonald CL et al (2011) Nogo receptor is involved in the adhesion of dendritic cells to myelin. J Neuroinflammation 8:113.
Miller DH et al (2012) Clinically isolated syndromes. Lancet Neurol 11(2):157-169.
Natelson BH et al (2005) Spinal fluid abnormalities in patients with chronic fatigue syndrome. Clin Diagn Lab Immunol 12(1):52-55.
Peng X et al (2010) Soluble Nogo receptor down-regulates expression of neuronal Nogo-A to enhance axonal regeneration. J Biol Chem 285(4): 2783-2795.
Petratos S et al (2012) Limiting multiple sclerosis related axonopathy by blocking Nogo receptor and CRMP-2 phosphorylation. Brain 135:1794-1818.
Satoh J et al (2004) The 14-3-3 protein epsilon isoform expressed in reactive astrocytes in demyelinating lesions of multiple sclerosis binds to vimentin and glial fibrillary acidic protein in cultured human astrocytes. Am J Pathol 165(2):577-592.
Schutzer SE et al (2010) Establishing the proteome of normal human cerebrospinal fluid. PLoS One 5: e10980, pp. 1-7.
Schutzer SE et at (2011) Distinct cerebrospinal fluid proteomes differentiate post-treatment Lyme disease from chronic fatigue syndrome. PLoS One 6(2): e17287, pp. 1-8.
Schutzer SE et al (2013) Gray matter is targeted in first-attack multiple sclerosis. PLoS One 8(9):e66117, pp. 1-7.
Steinman L (2009) The gray aspects of white matter disease in multiple sclerosis. Proc Natl Acad Sci USA 106(20): 8083-8084.
Tumani H et al (1995) Relevance of cerebrospinal fluid variables for early diagnosis of neuroborreliosis. Neurology 45(9):1663-1670.
Tumani H et al (2009) CSF proteome analysis in clinically isolated syndrome (CIS): candidate markers for conversion to definite multiple sclerosis. Neurosci Lett 452: 214-217.
Wang X et al (2011) Recovery from chronic spinal cord contusion after Nogo receptor intervention. Ann Neurol 70(5):805-821.
Zhang J et al (2005) Quantitative proteomic analysis of age-related changes in human cerebrospinal fluid Neurobiol Aging 26(2):207-227.

* cited by examiner

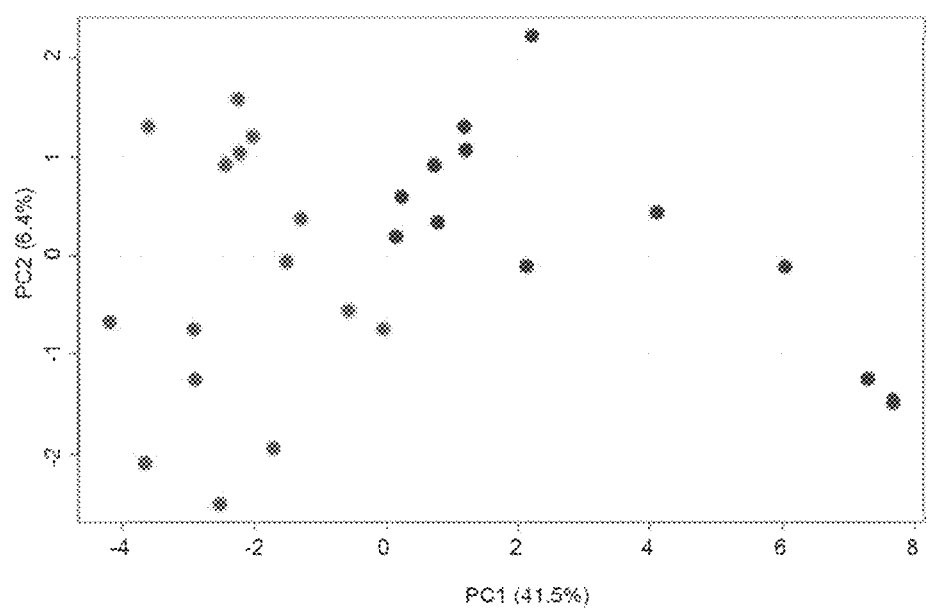

Figure 3 (Table 1a)

| IPI | Gene | Protein name | Fold change | | | Function |
|---|---|---|---|---|---|---|
| | | | First-attack CIS vs. RR | First-attack CIS vs. Control | Established RR vs. Control | |
| IPI00289204 | RTN4R | Nogo receptor | 8.04 | 2.62 | -3.07 | Regulates axonal growth, regeneration, synaptic recovery; decreases amyloid beta levels |
| IPI00023845 | KLK6 | Kallikrein-6 (Neurosin) | 2.79 | 1.06 | -2.64 | Serine protease, produced by activated macrophages, active against extracellular matrix, amyloid precursor protein, myelin basic protein, alpha synuclein. |
| IPI00011605 | CBLN1 | Cerebellin-1 | 2.67 | 1.46 | -1.83 | Synapse integrity, plasticity, stimulates norepinephrine release |
| IPI00017601 | CP | Ceruloplasmin | 1.78 | 1.7 | -1.05 | Iron transport, binds copper |
| IPI00002714 | DKK3 | Dickkopf-3 (RIG-like 7-1) | 1.78 | 1.12 | -1.59 | Affects synapse formation, signaling |
| IPI00020012 | APLP1 | Amyloid beta precursor-like protein 1 | 1.68 | 0.97 | -1.73 | Involved in synapse maturation, postsynaptic function, neurite outgrowth. |
| IPI00015102 | ALCAM | Activated leukocyte cell adhesion molecule (CD166) | 1.45 | 1.16 | -1.24 | Neurite extension, controls MMP-2 activation, expressed on neurons, activated T and B cells, monocytes. |
| IPI00376427 | NCAM2 | Neural cell adhesion molecule 2 | 2.34 | 1.05 | -2.24 | Type 1 membrane glycoprotein, implicated in interneuronal and glia-neuronal adhesion, reparative and remyelinating activity. |
| IPI00015260 | NELL2 | Neural epidermal growth factor like 2/ cerebral protein-12 | 2.12 | 1.54 | -1.38 | Secreted glycoprotein involved in neural cell growth and differentiation. |

Figure 4 (Table 1b)

| IPI | Gene | Protein name | Fold change | | | Function |
|---|---|---|---|---|---|---|
| | | | First-attack CIS vs. RR | First-attack CIS vs. Control | Established RR vs. Control | |
| IPI00291262 | CLU | Clusterin (Apolipoprotein J, complement lysis inhibitor) | -1.07 | -1.65 | -1.54 | Secreted chaperone, involved in protein folding/aggregation, clearance of misfolded proteins, protects against apoptosis and complement cytolysis. |
| IPI00456623 | BCAN | Brevican | -1.14 | -2.25 | -1.98 | Brain specific proteoglycan involved in cortical CNS development. |
| IPI00290085 | CDH2 | Neuronal cadherin | -1.6 | -2.14 | -1.34 | Synapse adhesion, axon outgrowth and guidance, neuronal recognition, dendritic spine density, adhesion molecule. |
| IPI00002147 | CHI3L1 | Chitinase-3-like 1 protein | -2.81 | -1.43 | 1.97 | Secreted by activated macrophages; plays role in response to pathogens, ability of cell to respond to microenvironment. |
| IPI00472011 | NEO1 | Neogenin | -2.83 | -1.94 | 1.46 | Transmembrane receptor involved in neuronal differentiation, apoptosis, repulsive axon guidance, cell adhesion mechanisms. |

Figure 5 (Table 1c)

| IPI | Gene | Protein name | Fold change | | | Function |
|---|---|---|---|---|---|---|
| | | | First-attack CIS vs. RR | First-attack CIS vs. Control | Established RR vs. Control | |
| IPI00022822 | COL18A1 | Collagen alpha 1 (XVIII) chain, Endostatin | 3.11 | -1.45 | -4.51 | Extracellular matrix protein, antiangiogenic |
| IPI00028911 | DAG1 | Dystroglycan 1 | 2.02 | -1.06 | -2.15 | Laminin binding component,scaffolds axin to cytoskeleton,cell adhesion receptor. |
| IPI00024956 | CNTN2 | Contactin 2 | 1.7 | -1.17 | -1.99 | Neuronal membrane protein that functions as adhesion molecule,involved in axonal connections, expressed on axons and juxtaparanodal region of myelinating oligodendrocytes. |
| IPI00008318 | EPHA4 | Ephrin type A receptor 4 | 1.4 | -1.05 | -1.46 | Member of protein-tyrosine kinase family, involved in signal transduction,axon and dendritic development. |
| IPI00783390 | CHL1 | Neural cell adhesion molecule L1 like protein | 1.3 | -1.17 | -1.52 | Neural recognition molecule involved insignal transduction, synaptic plasticity, neurtote outgrowth, suppresses neuronal death. |
| IPI00029751 | CNTN1 | Contactin 1 | 1.14 | -1.45 | -1.65 | Neuronal membrane protein, axon-myelinating glial cell signaling, oligodendrocyte generation via NOTCH 1 ligand. |

DIAGNOSTIC MARKERS FOR MULTIPLE SCLEROSIS

CROSS REFERENCE TO RELATED APPLICATIONS

The present application is a National Stage Application which claims priority under 35 USC § 120 from co-pending PCT Application No. PCT/US2014/051215, filed Aug. 15, 2014, which in turn claims priority under 35 USC § 119(e) from U.S. Provisional Application Ser. No. 61/866,319, filed Aug. 15, 2013, each of which applications is herein specifically incorporated by reference in its entirety.

GOVERNMENTAL SUPPORT

The research leading to the present invention was funded in part by the National Institutes of Health, through NIAID grant AI088765, NIDA grant DA021071, National Center for Research Resources grant 5 P41 RR018522-10 and National Institute of General Medical Sciences grant 8 P41 GM103493-10. The United States government has certain rights in the invention.

FIELD OF THE INVENTION

The present invention relates to identifying biologic markers (biomarkers) that can be used for diagnosis of multiple sclerosis (MS). In a more particular aspect, the invention pertains to the identification of a biomarker signature that is diagnostic for multiple sclerosis and methods for use of the MS diagnostic signature. Accordingly, the invention further relates to a method for diagnosing a person or other mammal with MS, or at risk for developing same. The biomarkers and diagnostic signatures described herein also identify metabolic/biochemical pathways as potential candidates for therapeutic targeting. The invention further relates to guidance pertaining to appropriate treatment for the person or mammal diagnosed with MS in accordance the methods described herein. Accurate diagnosis of neuropsychiatric disease, particularly with respect to diseases that are difficult to distinguish clinically, should reduce the duration and/or severity of the disease by ensuring that the patient is treated using an appropriate therapeutic regimen.

BACKGROUND OF THE INVENTION

Multiple sclerosis is a debilitating disease that is difficult to diagnose definitively, especially during the early stages of the disease. Multiple sclerosis is a common demyelinating disease of the central nervous system (CNS) that affects up to 0.1% of the Caucasian population of northern European descent. Multiple sclerosis is more common in women than men and generally begins between ages 20 and 40, but can develop at any age. Multiple sclerosis is generally viewed as an autoimmune syndrome directed against unidentified central nervous tissue antigens. The determination of susceptibility to multiple sclerosis development is complex and appears to be governed by both environmental and genetic factors. Some of the symptoms of multiple sclerosis are caused by damage to the myelin sheath, the protective covering that surrounds nerve cells. When this nerve covering is damaged, nerve impulses are slowed down or stopped. Ultimately, damage to the myelin sheath results in nerve damage. Nerve damage may be caused by inflammation that occurs when the body's immune cells attack the nervous system. Repeated episodes of inflammation can occur along any area of the brain and spinal cord, which is why the disease is often referred to as one characterized by symptoms and signs over time and space.

Multiple sclerosis is difficult to diagnose because the progress, severity and specific symptoms of multiple sclerosis are quite variable and unpredictable. There are no laboratory tests, symptoms or physical findings that can singly determine if a person has multiple sclerosis. The differential diagnosis of multiple sclerosis is quite varied and includes metabolic, genetic, oncologic, immunologic, and infectious disease assessment. Other diseases that may need to be considered in the differential diagnoses, depending on the clinical presentation, include: Acute disseminated encephalomyelitis, CNS vasculitis, Behçet disease, Sjögren syndrome, Sarcoid, neoplasms, CADASIL (cerebral autosomal dominant arteriopathy with subcortical infarcts and leukoencephalopathy), Migrainous ischemia, Cerebrovascular disease, Progressive multifocal leukoencephalopathy, Inherited white matter diseases, effects of radiation therapy or drugs, CNS lymphoma, Lyme disease, HTLV-1 infection, CNS lupus, Mitochondrial encephalopathies, Antiphospholipid antibody syndrome, cerebral emboli, Thrombocytopenic purpura, Progressive multifocal leukoencephalopathy, Mycoplasma encephalopathy, Vitamin B12 deficiency, Paraneoplastic syndromes, Psychiatric syndromes (Rolak L A, Fleming J O. The Neurologist 2007; 13: 57-72).

Over the last twenty years, tests such as magnetic resonance imaging (MRI), examination of CSF, and evoked response testing have played an increasingly important role in the diagnostic process. In 2005, revised McDonald criteria for multiple sclerosis were published (Polman et al. Diagnostic Criteria for Multiple Sclerosis: 2005 Revisions to the "McDonald" Criteria. Ann Neurol. (2005) 58:840-846 and Polman et al. Ann Neurol (2011) 69:292-302). In addition to the traditional diagnostic tools, the revised criteria provide specific guidelines for using findings of MRI, cerebrospinal fluid analysis and visual evoked potentials to support a diagnosis of multiple sclerosis. However, even with these revised criteria, diagnosis of multiple sclerosis is still challenging and frequently takes several months or even years.

Rendering a conclusive diagnosis of multiple sclerosis on an expedited basis would be of great benefit to patients in light of the potential for recurrence of attacks and progression of the disease. Drugs for the treatment of multiple sclerosis are now available which slow or prevent progression of the disease in many patients, and an early diagnosis would, therefore, allow early intervention and could significantly improve the quality of life for many multiple sclerosis patients.

The citation of references herein shall not be construed as an admission that such is prior art to the present invention. Several publications and patent documents are referenced in this application in order to more fully describe the state of the art to which this invention pertains. The disclosure of each of these publications and documents is incorporated by reference herein.

Other features and advantages of the invention will be apparent from the detailed description, the drawings, and the claims.

SUMMARY OF THE INVENTION

The cause or causes of MS, its driving pathogenesis at the earliest stages, and what factors allow the first clinical attack to manifest remain unknown. Some imaging studies suggest that gray rather than white matter may be involved early and may be predictive of developing MS, but other imaging studies dispute this suggestion. To determine if objective molecular evidence of gray matter involvement in early MS exists, the present inventor used high-resolution mass spectrometry to identify proteins in the cerebrospinal fluid (CSF) of first-attack MS patients (two independent groups), as compared to established relapsing remitting (RR) MS and controls. The present inventor found that the CSF proteins in first-attack patients were differentially enriched for gray matter components (elements of axons, neurons, synapses). In contrast, myelin components characteristic of white matter did not distinguish these groups. Accordingly, results presented herein support the position that gray matter dysfunction is involved early in MS, and also may be integral for the initial clinical presentation.

Accordingly, in a first aspect, a method for diagnosing first-attack multiple sclerosis in a patient is encompassed herein, the method comprising: a) isolating a cerebrospinal fluid (CSF) sample from the patient; and b) contacting the CSF sample with reagents specific for each of a panel of biomarkers to assess expression of the biomarkers, wherein the panel of biomarkers consists of or comprises Neural epidermal growth factor like 2/cerebral protein-12, Cerebellin-1, Nogo receptor, Dickkopf-3 (RIG-like 7-1), Brevican, Chitinase-3-like 1 protein, and Neogenin; and c) comparing expression of each of the biomarkers in the CSF sample to expression of each of the biomarkers, respectively, in a control CSF sample to determine if expression of any of the biomarkers in the CSF sample is increased or decreased relative to biomarkers in the control CSF sample, wherein detection of increased expression of at least one of Neural epidermal growth factor like 2/cerebral protein-12, Cerebellin-1, Nogo receptor, or Dickkopf-3 (RIG-like 7-1) in the CSF sample relative to expression for each biomarker, respectively, in a control CSF sample is a positive indicator of first-attack multiple sclerosis in the patient; and detection of decreased expression of at least one of Brevican, Chitinase-3-like 1 protein, or Neogenin in the CSF sample relative to expression for each biomarker, respectively, in a control CSF sample is a positive indicator of first-attack multiple sclerosis in the patient, and identification of at least two positive indicators in the patient serves to diagnose the patient as a first-attack multiple sclerosis patient. With regard to the first aspect, the at least two positive indicators refer, relate, or correspond to increased or decreased expression of two, three, four, five, six, or seven of the biomarkers in the CSF sample relative to the control CSF sample.

Also encompassed herein in a second aspect is a method for diagnosing first-attack multiple sclerosis in a patient, the method comprising: a) isolating a cerebrospinal fluid (CSF) sample from the patient; and b) contacting the CSF sample with reagents specific for each of a panel of biomarkers to assess expression of the biomarkers, wherein the panel of biomarkers consists of or comprises Neural epidermal growth factor like 2/cerebral protein-12, Cerebellin-1, Neural cell adhesion molecule 2, and Neuronal cadherin; and c) comparing expression of each of the biomarkers in the CSF sample to expression of each of the biomarkers, respectively, in a control CSF sample to determine if expression of any of the biomarkers in the CSF sample is increased or decreased relative to biomarkers in the control CSF sample, wherein detection of increased expression of at least one of Neural epidermal growth factor like 2/cerebral protein-12, Cerebellin-1, or Neural cell adhesion molecule 2 in the CSF sample relative to expression for each biomarker, respectively, in a control CSF sample is a positive indicator of first-attack multiple sclerosis in the patient; and detection of decreased expression of Neuronal cadherin in the CSF sample relative to Neuronal cadherin expression in a control CSF sample is a positive indicator of first-attack multiple sclerosis in the patient, and identification of at least two positive indicators in the patient serves to diagnose the patient as a first-attack multiple sclerosis patient. With regard to the second aspect, the at least two positive indicators refer, relate, or correspond to increased or decreased expression of two, three, or four of the biomarkers in the CSF sample relative to the control CSF sample.

Although an exemplary biological sample is set forth with respect to CSF, it is to be understood that other biological samples, including blood or a component thereof (e.g., plasma, serum, cells), tissue or tissue-related fluids, urine, or saliva may be assessed using methods described herein. This applies to any of the methods described herein.

In a particular embodiment, the reagents specific for each of the panel of biomarkers comprise antibodies. In a further aspect thereof, the antibodies are tagged antibodies.

In another particular embodiment, the at least one biomarker increased or decreased in the CSF sample is two, three, or four biomarkers.

In yet another embodiment, the method further comprises processing the CSF sample prior to step b. As described herein, processing may comprise immunodepletion of abundant proteins and sample concentration. Immunodepletion assists in removal of abundant proteins that may potentially obscure identification of less abundant proteins in the sample. The processing step may comprise proteolytic enzymatic digestion with or without immunodepletion.

In a particular embodiment of either of the first or second aspect, the at least two positive indicators comprise increased expression of Neural epidermal growth factor like 2/cerebral protein-12 and Cerebellin-1.

In a particular embodiment of the second aspect, the method may further comprise contacting the CSF sample with a reagent specific for Chitinase-3-like 1 protein to assess Chitinase-3-like 1 protein expression in the CSF sample and comparing expression of Chitinase-3-like 1 protein in the CSF sample to expression of Chitinase-3-like 1 protein in the control CSF sample to determine if expression of Chitinase-3-like 1 protein is decreased in the CSF sample relative to Chitinase-3-like 1 protein expression in the control CSF sample, wherein decreased expression in the CSF sample relative to expression in control CSF samples is a positive indicator of first-attack multiple sclerosis in the patient. The additional analysis serves to provide yet another positive indicator, thereby affirming and strengthening the initial assessment and diagnosis.

In yet another embodiment, the method may further comprise contacting the CSF sample with reagents specific for additional biomarkers consisting of Nogo receptor, Kallikrein-6 (Neurosin), Ceruloplasmin, Dickkopf-3 (RIG-like 7-1), Activated leukocyte cell adhesion molecule (CD166), Clusterin (Apolipoprotein J, complement lysis inhibitor), Brevican, Neogenin, Multifunctional protein MFP (collagen alpha 1 18) chain, Endostatin), Dystroglycan 1, Contactin 2, Ephrin type A receptor 4, Neural cell adhesion molecule L1 like protein, and Contactin 1 to assess expression of each of the additional biomarkers and comparing expression of each of the additional biomarkers in the CSF sample to expression of each of the additional biomarkers, respectively, in a control CSF sample to determine if expression of any of the additional biomarkers in the CSF sample is increased or decreased relative to the additional biomarkers in the control CSF sample, wherein detection of increased expression of any one of Nogo receptor, Kallikrein-6 (Neurosin), Ceruloplasmin, Dickkopf-3 (RIG-like 7-1), or Activated leukocyte cell adhesion molecule (CD166) in the CSF sample relative to expression for each protein, respectively, in control CSF samples is a positive indicator of first-attack multiple sclerosis in the patient; and detection of decreased expression of any one of Clusterin (Apolipoprotein J, complement lysis inhibitor), Brevican, Neogenin, Multifunctional protein MFP (collagen alpha 1 18) chain, Endostatin), Dystroglycan 1, Contactin 2, Ephrin type A receptor 4, Neural cell adhesion molecule L1 like protein, or Contactin 1 in the CSF sample relative to expression for each protein, respectively, in control CSF samples is a positive indicator of first-attack multiple sclerosis in the patient. Such additional analyses serve to provide additional positive indicators, thereby affirming and strengthening the initial assessment and diagnosis.

In a particular embodiment of either the first or second aspect, the increase or decrease is at least about a fold change of 1.1 or 1.2.

The method may be performed in the context of a patient who has experienced one of the common initial symptoms of multiple sclerosis comprising weakness, imbalance, vision problems, or sensory problems. In a particular embodiment, the patient may have experienced a vision problem and, more particularly, optic neuritis.

In another embodiment of the first or second aspect, the method may further comprise administering to the patient diagnosed with first-attack multiple sclerosis a disease modifying agent for treating multiple sclerosis. The disease modifying agent for treating multiple sclerosis may be Aubagio (teriflunomide), Avonex (interferon beta-1a), Betaseron (interferon beta-1b), Copaxone (glatiramer acetate), Extavia (interferon beta-1b), Gilenya (fingolimod), Novantrone (mitoxantrone), Rebif (interferon beta-1a), Tecfidera (dimethyl fumarate), or Tysabri (natalizumab).

Also encompassed herein in a third aspect is a method for diagnosing first-attack multiple sclerosis in a patient, the method comprising: a) isolating a cerebrospinal fluid (CSF) sample from the patient; and b) contacting the CSF sample with reagents specific for each of a panel of biomarkers to assess expression of the biomarkers, wherein the panel of biomarkers consists of Neural epidermal growth factor like 2/cerebral protein-12, Cerebellin-1, Neural cell adhesion molecule 2, Neuronal cadherin, Nogo receptor, Kallikrein-6 (Neurosin), Ceruloplasmin, Dickkopf-3 (RIG-like 7-1), Activated leukocyte cell adhesion molecule (CD166), Clusterin (Apolipoprotein J, complement lysis inhibitor), Brevican, Chitinase-3-like 1 protein, Neogenin, Multifunctional protein MFP (collagen alpha 1 18) chain, Endostatin), Dystroglycan 1, Contactin 2, Ephrin type A receptor 4, Neural cell adhesion molecule L1 like protein, and Contactin 1 and comparing expression of each of the biomarkers in the CSF sample to expression of each of the biomarkers, respectively, in a control CSF sample to determine if expression of any of the biomarkers in the CSF sample is increased or decreased relative to biomarkers in the control CSF sample, wherein detection of increased expression of at least one of Neural epidermal growth factor like 2/cerebral protein-12, Cerebellin-1, Nogo receptor, or Dickkopf-3 (RIG-like 7-1) in the processed CSF sample relative to expression for each biomarker, respectively, in a processed control CSF sample is a positive indicator of first-attack multiple sclerosis in the patient; and detection of decreased expression of at least one of Brevican, Chitinase-3-like 1 protein, or Neogenin in the processed CSF sample relative to expression for Neuronal cadherin in a processed control CSF sample is a positive indicator of first-attack multiple sclerosis in the patient, and identification of at least two positive indicators in the patient serves to diagnose the patient as a first-attack multiple sclerosis patient. With regard to the third aspect, the at least two positive indicators refer, relate, or correspond to increased or decreased expression of two, three, four, five, six, or seven of the biomarkers in the CSF sample relative to the control CSF sample.

In a particular embodiment of the third aspect, the reagents specific for each of the panel of biomarkers comprise antibodies. In a further aspect thereof, the antibodies are tagged antibodies. In yet another embodiment, the method further comprises processing the CSF sample prior to step b. As described herein, processing may comprise immunodepletion of abundant proteins and sample concentration. The processing step may comprise proteolytic enzymatic digestion with or without immunodepletion. In a particular embodiment of the third aspect, the at least two positive indicators comprise increased expression of Neural epidermal growth factor like 2/cerebral protein-12 and Cerebellin-1. In another embodiment, the increase or decrease is at least about a fold change of 1.1 or 1.2. The method may, moreover, be performed in the context of a patient who has experienced one of the common initial symptoms of multiple sclerosis comprising weakness, imbalance, vision problems, or sensory problems. Such vision problems may comprise optic neuritis. In a further embodiment, the method may further comprise administering to the patient diagnosed with first-attack multiple sclerosis a disease modifying agent for treating multiple sclerosis. The disease modifying agent for treating multiple sclerosis may be Aubagio (teriflunomide), Avonex (interferon beta-1a), Betaseron (interferon beta-1b), Copaxone (glatiramer acetate), Extavia (interferon beta-1b), Gilenya (fingolimod), Novantrone (mitoxantrone), Rebif (interferon beta-1a), Tecfidera (dimethyl fumarate), or Tysabri (natalizumab).

Also encompassed herein, is a kit for diagnosing first-attack multiple sclerosis, wherein the kit comprises reagents for detecting expression of at least one biomarker a panel of biomarkers, wherein the panel of biomarkers consists of Neural epidermal growth factor like 2/cerebral protein-12, Cerebellin-1, Neural cell adhesion molecule 2, Neuronal cadherin, Nogo receptor, Kallikrein-6 (Neurosin), Ceruloplasmin, Dickkopf-3 (RIG-like 7-1), Activated leukocyte cell adhesion molecule (CD166), Clusterin (Apolipoprotein J, complement lysis inhibitor), Brevican, Chitinase-3-like 1 protein, Neogenin, Multifunctional protein MFP (collagen alpha 1 18) chain, Endostatin), Dystroglycan 1, Contactin 2, Ephrin type A receptor 4, Neural cell adhesion molecule L1 like protein, and Contactin 1; and instructional materials.

In another aspect, a kit for diagnosing first-attack multiple sclerosis comprises reagents for detecting expression of at least one biomarker of a panel of biomarkers, wherein the panel of biomarkers consists of or comprises Neural epidermal growth factor like 2/cerebral protein-12, Cerebellin-1, Nogo receptor, Dickkopf-3 (RIG-like 7-1), Brevican, Chitinase-3-like 1 protein, and Neogenin; and instructional materials. The kit may further comprise reagents for detecting expression of Neuronal cadherin, Neural cell adhesion molecule 2, Kallikrein-6 (Neurosin), Ceruloplasmin, Activated leukocyte cell adhesion molecule (CD166), Multifunctional protein MFP (collagen alpha 1 18) chain, Endostatin), Dystroglycan 1, and Ephrin type A receptor 4.

Kits described herein may encompass reagents that are antibodies. In certain embodiments, the antibodies are tagged antibodies. Kit reagents may be in solution or immobilized on a solid surface, for example, on a membrane, gene chip, or on beads. When immobilized on beads, the beads may be maintained and/or assayed in a liquid medium. Reagents of the kits may be immobilized on a solid surface.

The first, second, or third aspect of the methods described herein further provide for a multiple sclerosis disease modifying agent or a composition thereof for use in treating the patient diagnosed with first-attack multiple sclerosis, wherein the multiple sclerosis disease modifying agent or the composition thereof alleviates symptoms of the first-attack multiple sclerosis in the patient when administered to the patient in a therapeutically effective amount.

The first, second, or third aspect of the methods described herein further provide for use of a multiple sclerosis disease modifying agent in the preparation of a medicament for the treatment of the patient diagnosed with first-attack multiple sclerosis, wherein the medicament alleviates symptoms of the first-attack multiple sclerosis in the patient when administered to the patient Such multiple sclerosis disease modifying agents are known in the art and comprise Aubagio (teriflunomide), Avonex (interferon beta-1a), Betaseron (interferon beta-1b), Copaxone (glatiramer acetate), Extavia (interferon beta-1b), Gilenya (fingolimod), Novantrone (mitoxantrone), Rebif (interferon beta-1a), Tecfidera (dimethyl fumarate), and Tysabri (natalizumab).

Other features and advantages of the invention will be apparent from the following description of the particular embodiments thereof, and from the claims.

BRIEF DESCRIPTION OF THE DRAWINGS

FIGS. 2A and 2B shows label-free quantification of CSF proteins identified in patient and control samples. 2A) Following the 1D LC MS analysis of immunodepleted CSF samples we identified peptides referable to 86 proteins that show significant difference in abundance by ANOVA (p-value <0.05). 2B) Partial least squares analysis of quantified proteins demonstrates that these three groups (control, first-attack CIS MS, RR-MS) can be distinguished from one another considering the CSF proteome.

FIG. 3 presents Table 1a which reveals that significant CSF brain protein changes occur in first-attack CIS-MS vs. established RR-MS and Controls. The indicated proteins are increased in first attack CIS-MS vs. established RR-MS, Controls.

FIG. 4 presents Table 1b, wherein the indicated proteins are decreased in first-attack CIS-MS vs established RR-MS and Controls.

FIG. 5 presents Table 1c, wherein the indicated proteins are increased in first-attack CIS-MS vs established RR-MS, but decreased in first-attack CIS-MS vs Controls.

DETAILED DESCRIPTION OF THE INVENTION

Figure 1:
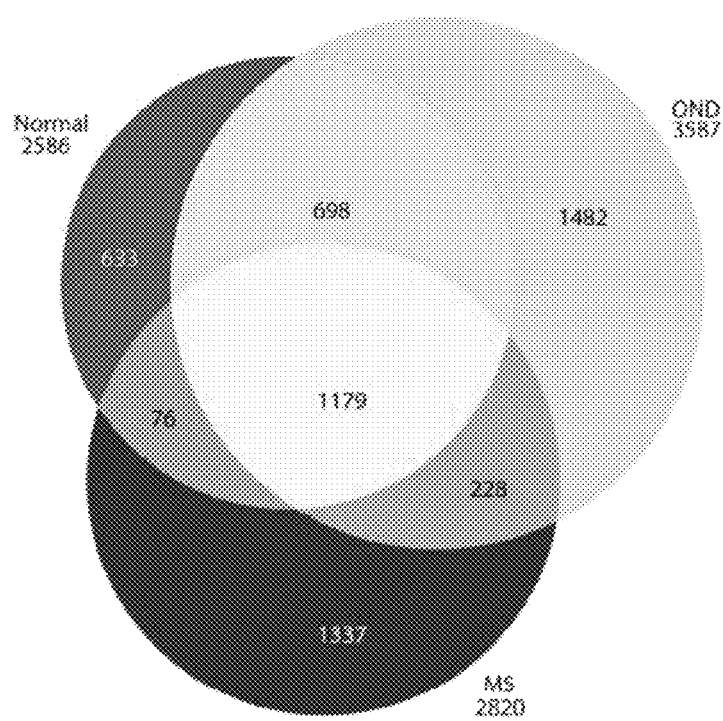
FIG. 1 shows an in-depth off-line 2D-LC-MS/MS analysis of the CSF proteome of a pooled sample comprised of CSF from all MS patients which resulted in the identification of 2820 proteins, and the comparison to previous results obtained from analyses of healthy normals[8] and other neurologic disease (OND) patients[9].

The cause of multiple sclerosis (MS)[1], its driving pathogenesis at the earliest stages, and how an area of the brain or spinal cord might be affected for the first clinical attack to manifest itself remain unknown. The first attack is a critical time-point to study in MS, since patients may be offered disease-modifying therapies once a definitive diagnosis has been made.

The most common MS clinical subtype is relapsing remitting MS (RR-MS), characterized by discrete attacks resulting in neurologic deficits. This is how 85% of MS patients present, with the first attack considered a clinically isolated syndrome (CIS)[2]. Many, but not all CIS-like attacks, turn out to be MS. The majority of patients are women. Compared to men the disease occurs two to three times more frequently in females and is on the rise among young women[3].

Some imaging studies suggest gray rather than white matter changes occur early, and predict the development of MS, but other imaging studies are in conflict with this position[2,4]

Cerebrospinal fluid (CSF) is an important body fluid to examine in MS because recent evidence suggests cell processing within the central nervous system (CNS) is a crucial component to the damage process. Meningeal and subarachnoid inflammation have been associated with cortical lesion development in very early MS patients[5,6]. CSF is known to reflect the CNS microenvironment, and is already used to document the presence of suggestive, although not conclusive, diagnostic immune abnormalities[7].

Mass spectrometry (this term is spelled out or if preceded by LC or if referring to tandem mass spectrometry it appears as MS, italicized to distinguish it from the disease multiple sclerosis which is abbreviated as MS non-italicized) based proteomics offers an effective tool to evaluate CSF proteins. Using advanced proteomic techniques, we have previously examined CSF collected from healthy controls[8], and two disease groups with confounding symptoms, chronic fatigue syndrome (CFS) and neurologic post treatment Lyme disease syndrome (nPTLS)[9]. The proteomic results permitted separation of one disease from another. With high abundant protein depletion, liquid chromatographic (LC) peptide fractionation, and sensitive mass spectrometry detection, we identified 2,630 nonredundant proteins in normal CSF[8]. This has been the most comprehensive CSF protein analysis to date, reflecting the great sensitivity of our methods.

In the current study, CSF collected during an attack from the earliest identifiable MS time-point was collected. CIS patients were confirmed as first-attack MS patients because they eventually met criteria for MS[10]. We compared the proteomic results to those from established RR-MS patients and controls (no overt neurologic disease). The goal was to determine whether the first-attack patients would have CSF proteins that could provide objective evidence to support or refute gray matter involvement in early MS. Results presented herein clearly support a role for gray matter involvement in early MS.

Results presented herein identify biomarkers and signatures diagnostic for MS in general and first attack MS in particular. See Example I and Tables 1a-c (FIGS. 3-5, respectively).

As indicated in each of Tables 1a-c, the present inventor has identified biomarkers, a relative fold increase or decrease of which as indicated herein is a positive indicator of first attack MS, for example, in a patient. Tables 1a-c reveal that significant CSF brain protein changes occur in first-attack CIS-MS vs. established RR-MS and Controls. Table 1a (FIG. 3), for example, sets forth a list of proteins that are increased in first attack CIS-MS vs. established RR-MS and Controls. Table 1b (FIG. 4) sets forth a list of proteins that are decreased in first-attack CIS-MS vs established RR-MS and Controls. Table 1c (FIG. 5) sets forth a list of proteins that are increased in first-attack CIS-MS vs established RR-MS, but decreased in first-attack CIS-MS vs Controls. Thus, a fold increase or decrease of at least one biomarker for first attack MS relative to control serves as a diagnostic tool for clinicians. A relative fold increase in at least one biomarker of a signature, such as that defined by Neural epidermal growth factor like 2/cerebral protein-12, Cerebellin-1, and Neural cell adhesion molecule 2, and also serves as a diagnostic tool. A further diagnostic tool is established by identifying a relative fold decrease in Neuronal cadherin. It is understood that a clinician will evaluate a patient as a whole based on known criteria well established in the field for diagnosis of MS and utilize the diagnostic method of the present invention in conjunction with such known diagnostic criteria to establish a definitive diagnosis.

It is to be understood that expression of biomarkers in control samples (e.g., control CSF samples) has been determined based on the guidance presented in the scientific literature and, more particularly, in accordance with Schutzer et al. (2013, PLoS 8:e66117), the entire content of which is incorporated herein by reference. Accordingly, methods described herein do not require a determination of biomarker expression in control samples, but rather only comparison to the pre-determined, established expression level of a biomarker in a control sample.

As used herein, the term "multiple sclerosis" is used to describe the art-recognized disease characterized by inflammation, demyelination, oligodendrocyte death, membrane damage, other neurologic damage, and axonal death. Multiple sclerosis can be characterized as one of four main varieties as defined in an international survey of neurologists (Lublin and Reingold, 1996, Neurology 46(4):907-11), which are namely: Relapsing-Remitting multiple sclerosis (RRMS), Primary Progressive multiple sclerosis (PPMS), Secondary-Progressive multiple sclerosis (SPMS), Progressive-Relapsing multiple sclerosis (PRMS).

As used herein, the terms "patient" or "subject" are used interchangeably. Such patients may have a neuropsychiatric disease or disorder, such as multiple sclerosis, and in particular first-attack multiple sclerosis. With respect to multiple sclerosis, for example, the terms "multiple sclerosis patient", "a subject who has multiple sclerosis", "a patient who has multiple sclerosis", "a multiple sclerosis subject", and similar phrases, are intended to refer to subjects who have been diagnosed with multiple sclerosis.

Typically, the first symptoms of MS appear gradually over hours or days, but symptoms may also begin precipitously. The most common initial symptoms of MS are: weakness, imbalance, vision problems, and sensory problems. Weakness may cause fatigue, difficulty walking, or trouble using fingers for fine movements or handling objects. Facial weakness may produce a drooping mouth, mimicking a stroke (ischemic, hemorrhagic) or Bell's palsy. Stiffness, which may be one-sided, and spasms often accompany the weakness. With respect to symptoms relating to imbalance, MS damage in the cerebellum and its connections can render individuals unable to walk in a straight line (heel to toe) or stand with both feet together without falling. These troubles become more severe when the individuals close their eyes. The imbalance can be accompanied by dizziness, which may cause vomiting. In severe cases, a person's speech may become slurred or "scanned," as he or she loses some capacity to articulate and coordinate the flow of words. Vision problems present in two forms. Optic neuritis manifests as a sudden difficulty reading, blurred vision in one eye, dimness, or inability to see red and other colors clearly. Many people feel pain around the affected eye. In this condition, MS has affected an optic nerve and the pathway that transmits images from the retina to the brain; in extreme cases, optic neuritis can produce blindness. The other type of visual disturbance is double vision, indicating damage to the nerve fibers in the brain stem that coordinate eye movements; the eyes cannot move together to focus on one image. The double vision disappears when the person with MS covers either eye. Sensory problems include tingling, pins and needles (paresthesias), pain, or numbness that can appear on the limbs, torso, or face. People with MS often describe abnormal sensations of swelling, squeezing, "water running on the skin," burning or cold, or "being wrapped." Some suffer trigeminal neuralgia, a recurrent shock-like pain in the temples and cheeks. Lhermitte's sign is another sensation like an electric shock that runs down the spine when one bends the neck forward; it can occur with several disorders of the spinal cord. See also The Dana Guide, Claude P. Genain and Stephen L. Hauser, March 2007, the entire content of which is incorporated herein by reference.

Further to the above, optic neuritis is a particularly noteworthy symptom of first-attack MS.

As used herein, the term "first-attack multiple sclerosis" refers to the first noticeable onset of clinical expression of the disease (appearance of MS compatible symptoms and/or signs). The timeframe in which the methods described herein may, therefore, be performed extends from initial onset of clinical expression of the disease up until radiological evidence generated via, for example, magnetic resonance imaging (MRI) is available that is consistent with the presence of MS. See, for example, the revised 2010 McDonald criteria in Polman et al. Diagnostic criteria for multiple sclerosis: 2010 revisions to the McDonald criteria. Ann Neurol 2011; 69:292-302, the entire content of which is incorporated herein by reference.

The terms "healthy subject", "normal subject", or "control subject", and similar phrases, are intended to refer to a subject who has not been diagnosed with a neuropsychiatric disease or disorder. A healthy subject has no other acute systemic disease or, at the least, has no detectable acute systemic disease. With respect to aspects of the invention directed to, for example, multiple sclerosis, the terms "healthy subject", "non-multiple sclerosis subject", "a subject who does not have multiple sclerosis", "a patient who does not have multiple sclerosis", and similar phrases, are intended to refer to a subject who has not been diagnosed with multiple sclerosis.

As used herein, the term "patient" or "subject" may refer to a mammal, including a human.

As used herein, the term "biological sample" includes a sample of any cell type or from any tissue or body fluid, body fluids including, but not limited to: cerebrospinal fluid (CSF), blood (whole blood, serum, plasma, or cellular components), saliva, urine, prostatic fluid, or fluid from any suitable tissue. In a particular embodiment, the biological sample is CSF. In another embodiment, the biological sample is blood or any component of blood (e.g., serum, plasma, cells, etc.).

The term "protein" is used herein to mean protein, polypeptide, oligopeptide or peptide. The terms "biologic marker", "biomarker" or "disease-associated protein" are used herein to refer to proteins associated with specific diseases or conditions, including proteins from organs or tissues ("organ-specific" or "tissue-specific" proteins) affected by a disease or condition. In accordance with the present invention, the increase or decrease in biomarker expression relative to that detected or characteristic of a subject/s without overt organic CNS disease or a normal, healthy subject/s (control/controls) is positively correlated with, indicative of, or diagnostic for the presence of a disease or condition, such as multiple sclerosis and particularly first-attack multiple sclerosis, in a patient.

As used herein, the terms "increase" or "decrease" in biomarker expression refer to a statistically significant increase or decrease, respectively. The term statistically significant is used in the art to refer to the likelihood that a result or relationship is caused by something other than mere random chance. Statistical hypothesis testing is traditionally employed to determine if a result is statistically significant or not. Such testing provides a "p-value" representing the probability that random chance could explain the result. In general, a 5% or lower p-value is considered to be statistically significant.

The present invention, furthermore, encompasses a plurality of biomarkers or a "biomarker signature" that is positively correlated with, indicative of, or diagnostic for the presence of a disease or condition, such as a neuropsychiatric disease, in a patient. Accordingly, a biomarker signature may also encompass a plurality of biomarkers that exhibit a relative increase or decrease in expression as compared to a healthy or normal subject (e.g., a control subject) and is positively correlated with, indicative of, or diagnostic for the presence of a disease or condition, such as a neuropsychiatric disease, in a patient.

A skilled practitioner would, moreover, appreciate that a relative increase or decrease in a particular protein (a biomarker) in a sample may be weakly indicative of disease, but not diagnostic, if noted as a single determinant. If, however, a plurality of such single determinants are noted in a biological sample, the combined detection of several weakly indicative determinants may serve to identify a strong combinatorial diagnostic indicator of disease. Furthermore, the single protein/determinant need not even approach the threshold of weak diagnostic by itself but in combination with the detection of an increase or decrease of another protein or proteins (other biomarkers) may serve as a strong combinatorial diagnostic indication of a disease state. Accordingly, also encompassed herein are combinatorial diagnostic indicators that are associated with a particular disease and not observed in healthy subjects or patients with other diseases.

Accordingly, selected sets of one, two, three, and more of the biomarkers of this invention (up to the number equivalent to all of the biomarkers, including any intervening number, in whole number increments, e.g., 1, 2, 3, 4, 5, 6 . . . ) can be used as diagnostic indicators for methods and/or in kits described herein. In one embodiment, larger numbers of the biomarkers identified herein are used in methods or kits of the invention, since the accuracy of the method or kit may improve as the number of biomarkers screened increases. With respect to aspects of the invention pertaining to evaluating therapeutic efficacy, the methods and kits of the present invention include evaluating whether administration of a therapeutic composition causes a change, either a transient change or a long term change, in expression of one or more of the biomarkers; in expression of two or more of the biomarkers; in expression of three or more of the biomarkers; in expression of four or more of the biomarkers; in expression of five or more of the biomarkers, in expression of six or more of the biomarkers, etc.

Representative permutations of biomarkers and/or biomarker signatures are presented herein below for illustrative purposes. Based on the methods described herein, a biological sample isolated from a subject may be determined to exhibit any one of the following biomarker signatures, which are set forth in exemplary fashion, and are not to be viewed as limiting: a+; a−; a+, b+, c+; or a+, b−, c+; wherein "a"=specific protein "a", "b"=specific protein "b", "c"=specific protein "c", etc. and "+" indicates that the protein is quantitatively increased relative to subjects without disease, which could be clinically normal or could have a different disease (e.g., a different disease having overlapping clinical symptoms which is, therefore difficult to distinguish) and "−" indicates that the protein is quantitatively decreased relative to subjects without disease, which could be clinically normal or could have a different disease (e.g., a different disease having overlapping clinical symptoms which is, therefore difficult to distinguish).

For example, the easiest identification of a protein biomarker is the presence of a protein associated with a disease or condition and not with other conditions that might be clinically confused with the disease under consideration. Variations to this scenario include the situation wherein a biomarker is present in an increased quantity or a decreased quantity compared to other conditions or controls. Although not a protein biomarker, an example of this is the presence of glucose in the blood in high quantities in diabetics compared to normal individuals who still have glucose present but not in elevated quantities. Another variation to the first scenario is where the functional biomarker is not just one protein but two or more in combination that can be quantitatively different, wherein the ensemble defines its biomarker potential.

In some embodiments, a biomarker of the invention is a member of a biological pathway. As used herein, the term "precursor" or "successor" refers to molecules that precede or follow the biomarker in the biological pathway. Thus, once a biomarker is identified as a member of one or more biological pathways, the present invention can include additional members of the biological pathway that come before (are upstream of or a precursor of) or follow (are downstream of) the biomarker. Such identification of biological pathways and their members is within the skill of one in the art.

Also encompassed herein is the analysis of biomarkers identified and listed in the tables presented herein to identify metabolic pathways implicated in the pathogenesis, maintenance, and/or progression of a disease. Such analyses may utilize a variety of software programs, including but not limited to the commercially available Ingenuity Pathway Analysis. Multiple hits in a particular metabolic pathway underscore the potential importance of the pathway for the disease and direct therapeutic intervention toward appropriate modulation of same. Accordingly, the present methods encompass such analyses and the identification of metabolic pathways of potential significance in a particular disease. Knowing that, for example, activation of a metabolic pathway appears to be linked or associated with a particular disease presents the opportunity to test pharmaceutical modulators of the pathway (i.e., inhibitors) to determine if such modulators could be used as therapeutics for treatment of patients with the disease.

Metabolic pathways may, for example, be associated with several disease conditions based on a quantitative assessment. Examples of pathways that may be markedly involved in one condition and not another or others may also be found.

Polypeptide biomarkers may be isolated by any suitable method known in the art. Native polypeptide biomarkers can be purified from natural sources by standard methods known in the art such as chromatography, centrifugation, differential solubility or immunoassay. In one embodiment, polypeptide and metabolite markers may be isolated from a biological sample using standard techniques known in the art, for example, chromatographic methods or affinity purification using substrate-bound antibodies that specifically bind to the marker. As described herein, immunoaffinity depletion of abundant proteins (with masking potential) enhances coverage and detection of low abundance proteins. As indicated herein above, depletion yields separate fractions that are characterized independently.

In a positively-associated example, once a protein or peptide is identified (including one lacking name identification, such as a hypothetical protein), a less expensive platform or assay, as compared to mass spectrometry, can be devised or adapted. The ELISA assay is such an example where an antibody to the biomarker protein/peptide can be used to capture the target biomarker in the biological sample being detected. The sample may be CSF or blood, etc. Variations of this immuno-based technique may also be used such as, but not limited to, Western blots wherein a sample comprising a biomarker is transferred to a membrane and then subsequently allowed to interact with specific antibodies that are coupled to an enzyme (later to be exposed to a substrate that permits colorimetric visualization) or fluorescent materials that permit visualization of one or more of the components or subcomponents (such as antigens) of the target biomarker. Alternatively, a non-coupled antibody can be used first and then a second antibody directed to this antibody, which has an enzyme or fluorescent tag attached thereto, can be used in a sandwich-like fashion. Another variation of this protein capturing technique could be multiplexing of several target biomarkers by using beads coated with multiple antibodies such as in the Luminex platform.

Antibodies immunospecific for any one of the biomarkers listed herein are available to the public and may be accessed via the scientific community or purchased from a commercial vendor. The worldwide web provides a readily searchable database for identifying potential suppliers for such antibodies. Santa Cruz Biotechnology, for example, offers for sale Nogo receptor antibodies (cat #s sc25659, sc16708, and sc16707), cerebellin-1 antibodies (cat # sc164050), neogenin antibodies (cat # sc6536), and Dystroglycan 1 antibodies (cat # sc 53987); Thermo Scientific, for example, offers for sale Pierce Antibody Products, including Neural epidermal growth factor like 2/cerebral protein-12 antibodies (cat # PA5-27958); Dickkopf-3 antibodies may be purchased from Lifespan Biosciences or Sino Biological; Chitinase-3-like 1 protein antibodies are available from R & D Systems; brevican, neogenin, and Dystroglycan 1 antibodies can be purchased from Abcam; and Ephrin type A receptor 4 antibodies can be purchased from Lifespan Biosciences or ECM Biosciences.

In another embodiment, once a disease protein/peptide biomarker is identified subsequent research may demonstrate that the body of a disease subject makes antibodies to the biomarker or biomarkers and the normal or other disease subject are negative for same. Under such circumstances, the presence of antibodies for a disease protein/peptide biomarker is indicative of disease. Experimentally, the presence of such disease specific antibodies is determined by using the disease protein/peptide biomarker as a binding target for the antibodies. This is a common indirect strategy for detection of infectious disease where the presence of an antibody indicates exposure to a foreign agent and in some cases the rise in titers (quantity of antibodies) over a short period of time indicates a very recent exposure.

As used herein, a polypeptide is referred to as "isolated" when it has been removed from its natural milieu (i.e., that has been subject to human manipulation), and can include purified polypeptides, partially purified polypeptides, synthetically produced polypeptides, and recombinantly produced polypeptides, for example. As such, "isolated" does not reflect the extent to which the polypeptide has been purified.

According to the present invention, the phrase "selectively binds to" refers to the ability of an antibody or antigen binding fragment thereof to preferentially bind to specified proteins. More specifically, the phrase "selectively binds" refers to the specific binding of one protein to another (e.g., an antibody or antigen binding fragment thereof to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen binding fragment thereof in the absence of the antigen is considered to be background. Binding can be measured using a variety of methods standard in the art including enzyme immunoassays (e.g., ELISA), immunoblot assays, etc.).

As used herein, the term "specifically binding," refers to the interaction between binding pairs such as an antibody and an antigen with an affinity constant of at most $10^{-6}$ moles/liter, at most $10^{-7}$ moles/liter, or at most $10^{-8}$ moles/liter.

The present invention includes the use of any of the biomarkers as described herein (including genes, cDNA, or their RNA or protein products), as targets for the development or identification of therapeutic compositions and strategies for the treatment of neuropsychiatric diseases, such as for example, multiple sclerosis, first-attack multiple sclerosis, and/or relapsing multiple sclerosis.

Methods to measure biomarkers of this invention, include, but are not limited to: Western blot, immunoblot, enzyme-linked immunosorbant assay (ELISA), radioimmunoassay (MA), immunoprecipitation, surface plasmon resonance, chemiluminescence, fluorescent polarization, phosphorescence, immunohistochemical analysis, liquid chromatography mass spectrometry (LC-MS), matrix-assisted laser desorption/ionization time-of-flight (MALDI-TOF) mass spectrometry, microcytometry, microarray, microscopy, fluorescence activated cell sorting (FACS), flow cytometry, laser scanning cytometry, hematology analyzer and assays based on a property of the protein including but not limited to DNA binding, ligand binding, or interaction with other protein partners. More particularly, high throughput, high sensitivity, and high resolution nanocapillary liquid chromatography-mass spectrometry (LC-MS), LC-MS/MS, pre-fractionation (immunoaffinity depletion chromatography) and ultra-high resolution nanocapillary LC separations, high efficiency ion transmission technologies (e.g., electrodynamic ion funnel), and the accurate mass and time (AMT) tag strategy for high-throughput analysis are described herein and known in the art.

As described herein, the term "probe" is used to refer to an agent that specifically binds to a biomarker listed in one of the tables presented herein. Suitable reagents for binding with a polypeptide corresponding to a biomarker of the invention include antibodies, antibody derivatives, labeled antibodies, antibody fragments, and the like. The term "probe" may also be used to refer to an agent that specifically binds to a nucleic acid sequence that encodes a biomarker listed in one of the tables presented herein. Suitable reagents for binding to a nucleic acid (e.g., a genomic DNA, an mRNA, a spliced mRNA, a cDNA, or the like) include complementary nucleic acids.

In accordance with the present disclosure, the tables present information with which an ordinarily skilled practitioner can access the amino acid sequences of the proteins identified herein as biomarkers, as well as nucleic acid sequences encoding same. A stepwise protocol for identification of the amino acid sequences listed in the tables presented herein is as follows: access one of the publicly available databases via the worldwide web, such as Uniprot knowledgebase (UniProtKB) and enter the IPI number, or the protein name, or the Gene designation. For example, the first protein listed in Table 1a is designated "Nogo receptor" and the corresponding Gene designation is RTN4R, with an IPI designation of IPI00289204. Entering the IPI number, protein name, or Gene into one of the above publicly available databases will reveal the amino acid sequence corresponding to "Nogo receptor". The above protocol is a matter of routine practice in laboratories skilled in the art and can be performed for any of the proteins listed therein. Such information may be used to design probes for detection of any of the proteins listed therein or to identify commercially available probes for detection of any of the proteins listed therein. Primers for detection nucleic acid sequences encoding any of the proteins listed in the tables presented herein are also envisioned. Such primers may be used to detect RNA expression levels (including relative increases or decreases as compared to controls) of a biomarker or biomarker signature of the invention. The design of primers for detecting expression levels of RNA (e.g., mRNA) of a biomarker or biomarkers listed herein is a matter of routine practice with the nucleic acid sequence in hand as provided by publicly available websites such as those mentioned above. Such probes and primers are useful for the kits described herein.

The present invention also includes a method to diagnose a subject as having first-attack multiple sclerosis. In one embodiment, the method includes the steps of isolating a cerebrospinal fluid (CSF) sample from the patient; and contacting the CSF sample with reagents specific for each of a panel of biomarkers to assess expression of the biomarkers, wherein the panel of biomarkers comprises Cerebellin-1, Neural cell adhesion molecule 2, Neural epidermal growth factor like 2/cerebral protein-12, and Neuronal cadherin; and thereby determine if expression of at least one of the biomarkers is increased or decreased in the CSF sample relative to expression for each of the at least one biomarkers, respectively, in a control CSF sample, wherein detection of increased expression of any one of Cerebellin-1, Neural cell adhesion molecule 2, or Neural epidermal growth factor like 2/cerebral protein-12 in the CSF sample relative to expression for each biomarker, respectively, in a control CSF sample is a positive indicator of first-attack multiple sclerosis in the patient; and detection of decreased expression of Neuronal cadherin in the CSF sample relative to Neuronal cadherin expression in a control CSF sample is a positive indicator of first-attack multiple sclerosis in the patient, and identification of at least one positive indicator in the patient serves to diagnose the patient as a first-attack multiple sclerosis patient. In a particular embodiment thereof, the patient or patient population is selected for assessment using the instant method based presentation of any one of the following clinical symptoms: vision problems weakness, imbalance, and sensory problems. The present invention further encompasses circumstances wherein there is a change in the level/amount of a biomarker described herein and such a change may also reflect responsiveness to a therapeutic regimen.

The invention includes a kit for assessing the expression of at least one of the biomarkers listed in the tables presented herein, whereby detecting the expression of at least one of the biomarkers in a biological sample isolated from a patient can be used to render a positive diagnosis of first-attack multiple sclerosis in the patient. The kit comprises a plurality of reagents, each of which is capable of binding specifically with a polypeptide (e.g., an antibody) or nucleic acid encoding same corresponding to a biomarker of the invention, e.g., one of the proteins listed in any one of the tables presented herein. Suitable reagents for binding with a polypeptide corresponding to a biomarker of the invention include antibodies, antibody derivatives, labeled antibodies, antibody fragments, and the like. Suitable reagents for binding to a nucleic acid (e.g., a genomic DNA, an mRNA, a spliced mRNA, a cDNA, or the like) include complementary nucleic acids. For example, the nucleic acid reagents may include oligonucleotides (labeled or non-labeled) fixed to a substrate, labeled oligonucleotides not bound with a substrate, pairs of PCR primers, molecular beacon probes, and the like.

The kit of the invention may optionally comprise additional components useful for performing the methods of the invention. By way of example, the kit may comprise fluids [e.g., phosphate buffered saline (PBS) or SSC buffer] suitable for binding an antibody to a protein for which it is immunologically specific or for annealing complementary nucleic acids, one or more sample compartments, an instructional material which describes performance of a method of the invention, a positive control or controls, such as panel of proteins corresponding one of the panels set forth in any one of the tables presented herein or a biological sample isolated from a normal subject (a subject who does not manifest clinical symptoms of disease), or a biological sample isolated from a patient known to have the disease in questions, and the like.

The following protocols are provided to facilitate the practice of the present invention.

The following examples are put forth so as to provide those of ordinary skill in the art with a complete disclosure and description of how to make and use the assay, screening, and therapeutic methods of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

EXAMPLE I

Methods and Materials

Ethics Statement

Approval for the conduct of this study was obtained from the Institutional Review Board of New Jersey Medical School, the Institutional Review Board of Pacific Northwest National Laboratory, the Human Ethics Committee at the Faculty of Medicine of Uppsala University, and the Human Investigation Review Board of the University of Szeged (in agreement with the Declaration of Helsinki). Written consent was obtained from subjects.

Introduction: Proteome Analysis of Cerebrospinal Fluid

Proteomics analysis of CSF samples faces two major analytical challenges: extremely high dynamic range in protein concentration (e.g., the top-14 most abundant proteins consist of ~95% of protein mass in CSF) and low overall protein concentration (i.e., typically 0.3 mg/mL, comparing to 60 mg/mL in blood plasma, under normal conditions). To maximize the findings possible from size-limited CSF sample sets, immunoaffinity depletion and the AMT tag strategy that combines both offline 2D-LC-MS/MS and direct LC-MS analyses were employed to provide both broad proteome coverage and reliable protein identification and quantitation. The offline 2D-LC-MS/MS analysis, where immunoaffinity-depleted CSF samples were fractionated into 30 fractions and each fraction was analyzed by highly sensitive LC-MS/MS on high-resolution Orbitrap Velos mass spectrometer, offers the broadest CSF proteome coverage. However, the use of immunoaffinity depletion and offline fractionation (30 fractions in this study) requires a large amount of starting material; hence it is best suited for deep profiling of the pooled MS sample for qualitative comparisons with the deep proteomes that were previously established for two ONDs and healthy controls. The direct LC-mass spectrometry analysis of individual CSF samples for label-free quantitation provides both high throughput measurements and good quantitation of relative protein abundance, and therefore uniquely suited for analysis of the entire set of individual CSF samples in the CIS, RR and control groups. Therefore, combining both the offline 2D-LC-MS/MS and direct LC-mass spectrometry analyses maximized the findings possible from size-limited CSF sample sets, contributing to truly comprehensive characterization of the CSF proteome in MS.

Subjects and Samples

We collected CSF from three subject groups with IRB approvals. Group 1 involved 9 first-attack CIS patients who eventually met the criteria for MS[10]. There were 8 females and 1 male, ranging in age from 18 to 42 years. Three had optic neuritis and 6 a multifocal CNS syndrome. Patients underwent lumbar puncture within 8 weeks of symptom onset. All had abnormal conventional brain MM suggestive for MS, and were shown to be CSF oligoclonal band positive. Group 2 involved 12 patients with established diagnosis of RR-MS by the 2005 McDonald criteria[10]. There were 9 females and 3 males, ranging in age from 19 to 47 years. Disease duration ranged from 3 months to 9 years. Seven underwent lumbar puncture within 8 weeks of a clinical relapse. All had abnormal brain MRI, and were shown to be CSF oligoclonal band positive. Group 3 involved 6 control subjects without overt organic CNS disease who underwent lumbar puncture for headache (n=5) or tinnitus (n=1). There were 4 females and 2 males, ranging in age from 31 to 54 years. In addition, for comparative purposes, we used previously published protein lists generated from 2 OND groups (CFS and neurologic PTLS,)[9], and more than 200 healthy and non-neurologic controls[8,9].

We analyzed a separate group of 10 patients with CIS-first-attack MS. Due to volume limitations, this analysis did not have the advantage of the current methods of immunoaffinity depletion of abundant proteins (which can mask less abundant proteins) and high fractionation of the sample. Nevertheless, this independent group permitted us to evaluate whether the gray matter proteins described in the Results in the immunoaffinity-depleted patients were also found in this group.

All CSF samples were immediately processed (cells spun out, and CSF aliquoted) and frozen at −80 C. RBC counts were less than 10 per $mm^3$.

Immunodepletion of Abundant Proteins from CSF

All CSF samples in the primary groups had the 14 most abundant proteins removed employing immunodepletion as previously described[8], increasing the depth of proteome coverage. Briefly, prior to immunodepletion CSF samples were concentrated as follows: a 2.0-mL CSF aliquot was concentrated with a Millipore Amicon Ultra-4 3000 MWCO filter (Fisher Scientific, Pittsburgh, Pa.) to a final volume of 100 μl. The concentrated samples were then depleted of the 14 most abundant proteins using an IgY14 LC5 depletion column from Sigma (St. Louis, Mo.), and the depleted and bound proteins were collected. The depleted CSF fractions were then concentrated using a Millipore Amicon Ultra-15 3000 MWCO filter, (Fisher Scientific, Pittsburgh, Pa.), to a final volume of ~200 μl. The bound fractions samples underwent a buffer exchange into 50 mM $NH_4HCO_3$ (Sigma, St. Louis, Mo.). The volume of the samples was then adjusted using 50 mM $NH_4HCO_3$ to ensure that all samples had the same volume for in-solution digestion.

Both the flow-through (lower abundance proteins) and bound fractions from the group pooled CSF samples were collected and processed identically by high-resolution two-dimensional liquid chromatography coupled to high performance tandem mass spectrometry (2D-LC-MS/MS) analysis. These analyses produced the in-depth characterization of the CSF proteome, and the combined results of abundant protein and less abundant protein fractions were used in the creation of an AMT tag database[25] for high throughput analysis of a larger number of individual subject samples using LC-mass spectrometry.

Protein Digestion

Proteins isolated from CSF were digested with trypsin and processed as previously described[8]. Briefly, solid urea (Sigma, St. Louis, Mo.) was added to each sample to a final concentration of 8M. The samples were incubated at 37° C. for 1 hour to denature the proteins. Following denaturation, the disulfide bonds were reduced using 10 mM DTT from Sigma (St. Louis, Mo.) for 1 hour at 37° C. Then the samples were alkylated with 40 mM iodoacetamide from Sigma, (St. Louis, Mo.) for 1 hour in the dark at 37° C. The samples were diluted 10× with 50 mM $NH_4HCO_3$. Following dilution, 1 mM $CaCl_2$ from Sigma (St. Louis, Mo.) was added. Sequencing grade modified trypsin from Promega (Madison, Wis.) was then added in a 1:50 trypsin-to-protein ration. The samples were incubated for 3 hour at 37° C. Following trypsin digestion and SPE clean-up utilizing C-18 SPE cartridges from Supelco (St. Louis, Mo.), samples were concentrated in a Speed-Vac and the final peptide concentration (BCA assay (Pierce, Rockford, Ill.) was determined. Lastly all tryptic digests were snap frozen in liquid nitrogen and stored at −80° C. until further processing and analysis.

High-pH Reversed-Phase LC Fractionation and LC-MS/MS Analysis

A total of 300 μg of tryptic peptides from both the IgY14 bound and flow-through fractions from the pooled MS CSF samples were fractionated by High pH reversed phase (HPRP) LC as previously described[26]. 30 HPRP fractions were collected and 20% of each fraction was injected for reversed-phase LC-MS/MS analysis. HPRP fractions of the IgY14 bound fraction samples were analyzed on an LTQ (ThermoFisher, San Jose, Calif.) linear ion trap, and HPRP fractions of the IgY14 flow-through fraction samples were analyzed on an LTQ-Orbitrap Velos (ThermoFisher) instrument, operated in data-dependent mode and same LC conditions as previously described[8]. Briefly, a custom HPLC system was configured using 65-mL Isco Model 65D syringe pumps (Isco, Lincoln, Nebr.), 2-position Valco valves (Valco Instruments, Houston, Tex.), and a PAL autosampler (Leap Technologies, Carrboro, N.C.) to allow for fully automated sample analysis across four separate HPLC columns. RP capillary HPLC columns were manufactured in-house by slurry packing 3 mm Jupiter C18 particles (Phenomenex, Torrance, Calif.) into a 70 cm×75 mm i.d. fused silica capillary tubing (Polymicro Technologies, Phoenix, Ariz.). An exponential HPLC gradient of 100 min (from 0-70% B) was used for each analysis, with mobile phases consisting of 0.1% formic acid in water (A) and 0.1% formic acid in ACN (B). Electrospray emitters were custom made using 150 um o.d.×20 um i.d. chemically etched fused silica[27]. The heated capillary temperature and spray voltage were 275° C. and 2.2 kV, respectively. Data was acquired for 100 min, beginning 65 min after sample injection and 15 min into gradient. Orbitrap spectra (AGC $1\times10^6$) were collected from 400-2000 m/z at a resolution of 30,000 while data dependent ion trap CID MS/MS (collision energy 35%, AGC $3\times10^4$) spectra were acquired for the ten most abundant ions. A dynamic exclusion time of 180 sec was used to discriminate against previously analyzed ions.

Direct Reversed-Phase Capillary LC-Mass Spectrometry Analysis

Label-free quantification of proteins in individual CSF samples was performed as previously described[8]. To analyze the unfractionated, individually immunodepleted CSF samples, the RPLC and LTQ-Orbitrap Velos mass spectrometer were operated under the similar conditions as described above except that the data dependent mode was set up so that full scan mass spectrometry spectra (m/z 400-2000) were acquired in the Orbitrap with resolution of 60,000 at m/z 400 (AGC $1\times10^6$) while MS/MS spectra were acquired for the six most abundant ions (however MS/MS data acquired here were not used for the quantitative analysis).

Data Analysis

The LTQ raw data from the pooled samples was extracted using Extract MSn (version 3.0; ThermoFisher) and analyzed with the SEQUEST algorithm (V27 revision 12; ThermoFisher) searching the MS/MS data against the human IPI database (Version 3.40). Precursor mass tolerance of 3 daltons and 1 dalton for MS/MS ion masses without an enzyme defined, as well as static carboxyamidomethylation of cysteine and dynamic oxidation of methionine were used for the database search. The LTQ-Orbitrap Velos MS/MS data were first processed by in-house software DeconMSn [28] accurately determining the monoisotopic mass and charge state of parent ions, followed by SEQUEST search against the IPI database in the same fashion as described above, with the exception that a 0.1-dalton mass tolerance for parent ion masses and 1 dalton mass tolerance for fragment ion masses were used. Data filtering criteria based on the mass spectrometry-GF score and precursor ion mass accuracy (+/−10 ppm) and cut offs were developed using the decoy database approach and applied for filtering the raw data to limit false positive identifications to <1% at the peptide level [29-31].

The AMT tag strategy[25] was used for label-free quantification of mass spectrometry features observed in the LTQ-Orbitrap Velos analysis of the individual CSF samples from control and MS samples. The filtered MS/MS peptide identifications obtained from the 2D-LC-MS/MS analyses of all pooled CSF samples were included in an AMT tag database with their theoretical mass and normalized elution time (NET; from 0 to 1) recorded. LC-mass spectrometry datasets were then analyzed by in-house software VIPER [32] that detects features in mass-NET space and assigned them to peptides in the AMT tag database [33]. False discovery rate was controlled by filtering results for an FDR<3% filtering by STAC score[34] and mass measurement accuracy within 10 ppm.

The resulting lists of peptides from 2D-LC-MS/MS or direct LC-mass spectrometry analysis were further processed by ProteinProphet software[35] to remove redundancy in protein identification.

Data normalization and quantification of the changes in protein abundance between the normal CIS-MS and RR-MS CSF samples were performed and visualized using in-house software DAnTE [36]. Briefly, peptide intensities from the LC-mass spectrometry analyses of the individual samples were log 2 transformed and normalized using a mean central tendency procedure. Peptide abundances from the individual samples were then "rolled up" to the protein level employing the R-rollup method (based on trends at peptide level) implemented in DAnTE. ANOVA, partial least squares (PLS) and clustering analyses were also performed using DAnTE.

Pathway Analysis of the data was performed with Ingenuity Pathways Analysis (Ingenuity Systems, see worldwide web site ingenuity.com), as we have done before[9]. Canonical pathway analysis identified the pathways from the Ingenuity Pathways Analysis library of canonical pathways that were most significant to the MS proteins identified. The significance of the associations was assessed with the Fisher's exact test.

Results

The CSF proteome analysis of first-attack MS patients presented herein, which uses two separate patient sets in multiple replicates, identifies proteins that distinguish these patients from both established RR-MS and controls. The data, moreover, provides credible evidence that gray matter is likely involved early in the MS process.

To gain a broad picture of what informative proteins are detectable in the CSF samples of MS patients, an in-depth analysis of the pooled immunoaffinity depleted CSF samples from all first-attack CIS MS plus established RR-MS patients (both the flow-through and bound immunoaffinity depletion fractions were subjected to offline 2D-LC-MS/MS analysis) was performed. The results were compared to CSF analysis from our published pooled healthy normals and pooled other neurologic diseases (ONDs) (i.e., CFS and nPTLS). We identified 2,820 proteins in MS CSF, compared to 2,586 proteins in normal CSF and 3,587 proteins in OND CSF (FIG. 1). There were 1,337 proteins unique to MS CSF, 633 proteins unique to healthy normal CSF, and 1,482 proteins unique to OND CSF.

Figure 2A:
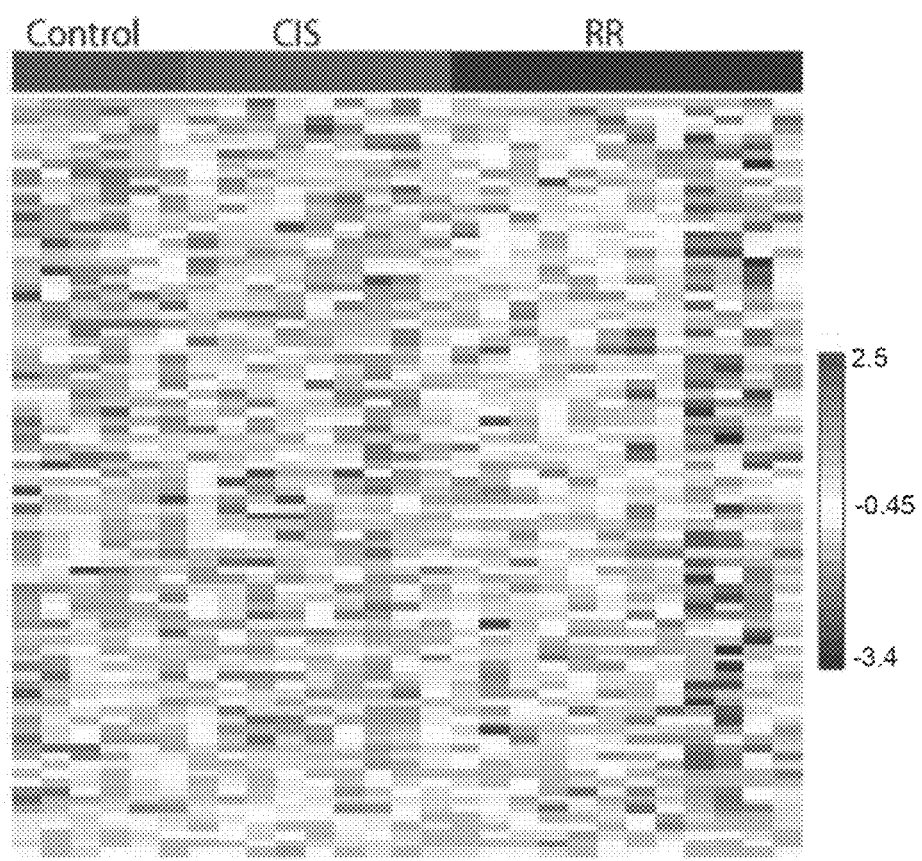

In order to compare quantitatively all CSF samples available from the three patient groups (CIS: n=9; RR: n=12; and control: n=6) and determine whether the CSF proteins could distinguish between groups, direct LC-mass spectrometry analysis of all the individually immunodepleted samples of the three groups (first-attack, established RR, and controls) included in the present study was performed, and peptide and protein abundances quantified employing the accurate mass and time (AMT) tag label-free quantification approach. The term direct preceding LC is used to emphasize that it was done without data-dependent MS/MS. The advantage of immunoaffinity depletion to remove obscuring high abundance proteins is apparent, because without depletion only 284 proteins were previously identified; following depletion, an average of 476 proteins was identified in direct LC-mass spectrometry analyses of the individual CSF samples in the three groups. FIG. 2B is the partial least squares analysis for the results from the label-free quantification of all the individual samples. This analysis displays good separation of the three groups applying the CSF proteome quantification results. Analysis of the quantitative differences in protein abundance comparing control, first-attack and established RR-MS samples revealed group specific differences in protein abundance. We performed a statistical test of variance of differences (ANOVA) across all data sets based on clinical diagnoses (e.g., Control, first-attack, established RR-MS), followed by unsupervised hierarchical clustering analysis of the statistically significant proteins (p-value<0.05) (see FIG. 2A).

The CNS-specific proteins detected in CSF were then selected, which revealed significant quantitative differences in the first-attack CIS MS group compared to established RR-MS and controls (Table 1a-c). There were a total of 20 such proteins. Nine were significantly increased in first-attack CIS MS compared to both groups. The most striking increase was in soluble Nogo receptor. Five proteins were significantly decreased in first-attack CIS MS compared to both other groups. Another six proteins were significantly increased in the first-attack CIS MS group compared to established RR-MS, but significantly decreased compared to levels in control CSF. At least 15 of these 20 proteins (75%) affect synapse, axon, and neuron functioning (gray matter associated), as opposed to myelin (white matter). Myelin proteins were detected in both established RR-MS and first-attack MS including myelin oligodendrocyte glycoprotein, myelin-associated glycoprotein, and proteolipid protein. These proteins did not, however, exhibit quantifiable differences in abundance. Neuronal related proteins, such as amyloid precursor protein, and neuronal adhesion molecules, such as NCAM, were also found among the 20 proteins. In another set of first-attack MS CSF samples that were previously profiled by offline 2D-LC-MS/MS (without applying immunodepletion due to sample size limitations), all the above 20 CNS-specific proteins were detected at significantly higher concentrations than the myelin proteins.

DISCUSSION

The proteomic data in the present study is consistent with imaging studies suggesting gray matter is involved in the early stages of MS. Interesting observations from data presented herein include the finding that the CSF proteome appears to distinguish first-attack MS from RR-MS and controls and that the first-attack MS CSF proteome is distinguished from RR-MS and control proteomes by gray matter component changes, not myelin component changes.

First-attack CIS-MS patients showed distinct CSF proteomes from those of established RR-MS and controls. The difference in proteins is not explainable by changes associated with having an attack, in and of itself, since the majority of the RR-MS cohort had their CSF obtained following an attack. Rather, these differences suggest a unique association with the first attack. It has been thought previously that MS relapses represent injury to eloquent areas of CNS[11], and the consequence of random formation of new macroscopic lesions (referred to pathologically as plaques, and visible on neuroimaging). Documentation of signature CSF proteins suggests that the first attack in MS may not be a random occurrence, but rather orchestrated by specific circumstances that culminate in clinical disease expression.

Careful CSF analysis should shed more light on the etiological factors associated with initiation of clinically apparent RR-MS. The first-attack MS patients showed identical patterns of increased and decreased quantities of proteins, different from established RR-MS patients (Table 1a-c).

The number of proteins referable to synapse, axon, and neuronal function that distinguish the first-attack MS group is striking. Nogo receptor, out of proportion to any other known protein, is markedly elevated in the CSF of first-attack patients compared to both RR-MS and controls. Nogo receptors regulate dendritic spine morphology. High expression of Nogo receptor has been associated with poorer synapse functioning[12]. Soluble Nogo receptor enhances axonal regeneration, and rescues retinal ganglion cells and synapses from injury in a chronic glaucoma model[13,14]. In a mouse model of chronic spinal cord injury, intrathecal injection of Nogo receptor enhanced axonal density and functional recovery[15]. Soluble Nogo, but not receptor, has been previously reported in the CSF of MS patients[16].

First-attack MS patients also showed a significant increase in their CSF of an axonal glycoprotein, contactin-2/TAG-1. This is a protein which earlier was reported as an autoimmune target in MS, with elevated levels of antibodies as well as T-cell responses in MS vs non-MS patients[17, 18]. There is an increasing literature on the importance of gray matter, neuronal and axonal involvement in MS, even at very early time-points[17]. The present findings corroborate and extend these findings, and indicate that axonal, neuronal and synaptic involvement may be required for the initial presentation of MS. It is interesting to note that in MS, a disease characterized by demyelination as it progresses, gray matter components may be diagnostically more useful than myelin components at the earliest stages.

Only four prior studies have performed proteomic analysis of CIS CSF samples. None of those studies, however, used techniques that approached the sensitivity of the current analysis. Tumani et al[19] evaluated CSF from a total of 16 CIS patients, half of whom developed disease activity in the next two years to qualify for a diagnosis of relapsing MS. They noted a total of 2,193 2-D DIGE gel spots; nine showed quantitative differences between the two groups. In our analysis none of these nine proteins were uniquely associated with first-attack MS (CIS) versus established RR-MS.

Comabella et al.[20] screened pooled CSF from 30 CIS patients who were oligoclonal band negative in CSF, with normal brain MRI maintained over one to five years (non-MS CIS); and 30 CIS patients with oligoclonal band positivity, abnormal brain MRI, and conversion to clinically definite MS over the next five years. In their paper, the CIS group is much more likely not to have MS. They identified a total of 267 proteins. The CIS-MS group showed differential expression of 23 proteins, with 17 upregulated and 6 downregulated. They then chose the three most consistently represented for validation (ceruloplasmin, vitamin D binding protein, chitinase-3-like protein 1). Only chitinase-3-like protein 1 could be "validated" by ELISA in additional patients. The present results confirm elevated ceruloplasmin in the CIS cohort, but actually found chitinase-3-like protein to be significantly decreased in CIS. Kroksveen et al[21] also reported similar data to that of the present study with respect to myelin related proteins not detected, or not differentiating, first-attack MS from established RR-MS.

Dhaunchak et al. evaluated 8 CIS pediatric patients who turned out to have RR-MS, and identified 67 proteins that differed from the non RR-MS group[22]. Of the top 16 such proteins, 20% dealt with the axoglial apparatus. They concluded that perturbed axoglial interactions must be involved in the early pathogenesis of MS. This study is not directly comparable, since it focused on pediatric patients, and did not compare first attack to established MS. Nevertheless it also linked gray matter rather than myelin components to CIS.

The present application of immunoaffinity depletion and the AMT tag strategy combining both offline 2D-LC-MS/MS (on pooled multiple sclerosis samples) and direct LC-MS analyses (on individual samples from the three groups) [23] on high-sensitivity nanoLC coupled to high-resolution mass spectrometers led to both broad proteome coverage and reliable protein identification and quantitation. The experimental approach maximized the findings possible from size-limited CSF sample sets, contributing to truly comprehensive characterization of the CSF proteome in MS. The same strategy has recently led to the identification of disease-specific CSF proteins which differentiate CFS from nPTLS, as well as from healthy control CSF[9], demonstrating its effectiveness in proteomic investigations in biofluids.

Although the use of the present mass spectrometry based proteomics method was for research purposes, they may have added value to current magnetic resonance imaging (MRI) because conventional MRI generally does not detect gray matter lesions. That requires non conventional advanced imaging technologies[24]

The present investigation sets forth intriguing findings which suggest that the CIS/true first-attack presentation of MS may not be random. The data also indicate that the CSF proteome of these patients is distinguishable from established RR-MS, particularly by gray matter components (axon, neuron, synapse), and that gray matter rather than myelin is more proximally involved in the initiation of MS.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

REFERENCES

1. Noseworthy J H, Lucchinetti C, Rodriguez M, Weinshenker B G (2000) Multiple sclerosis. N Engl J Med 343: 938-952.
2. Miller D H, Chard D T, Ciccarelli O (2012) Clinically isolated syndromes. Lancet Neurol 11: 157-169.
3. Greer J M, McCombe P A (2011) Role of gender in multiple sclerosis: clinical effects and potential molecular mechanisms. J Neuroimmunol 234: 7-18.
4. Calabrese M, Rinaldi F, Mattisi I, Bernardi V, Favaretto A, et al. (2011) The predictive value of gray matter atrophy in clinically isolated syndromes. Neurology 77: 257-263.
5. Lucchinetti C F, Popescu B F, Bunyan R F, Moll N M, Roemer S F, et al. (2011) Inflammatory cortical demyelination in early multiple sclerosis. N Engl J Med 365: 2188-2197.
6. Kivisakk P, Imitola J, Rasmussen S, Elyaman W, Zhu B, et al. (2009) Localizing central nervous system immune surveillance: meningeal antigen-presenting cells activate T cells during experimental autoimmune encephalomyelitis. Ann Neurol 65: 457-469.
7. Freedman M S, Thompson E J, Deisenhammer F, Giovannoni G, Grimsley G, et al. (2005) Recommended standard of cerebrospinal fluid analysis in the diagnosis of multiple sclerosis: a consensus statement. Arch Neurol 62: 865-870.
8. Schutzer S E, Liu T, Natelson B H, Angel T E, Schepmoes A A, et al. (2010) Establishing the proteome of normal human cerebrospinal fluid. PLoS ONE 5: e10980.
9. Schutzer S E, Angel T E, Liu T, Schepmoes A A, Claus T R, et al. (2011) Distinct cerebrospinal fluid proteomes differentiate post-treatment lyme disease from chronic fatigue syndrome. PLoS ONE 6: e17287.
10. Polman C H, Reingold S C, Edan G, Filippi M, Hartung H P, et al. (2005) Diagnostic criteria for multiple sclerosis: 2005 revisions to the "McDonald Criteria". Ann Neurol 58: 840-846.
11. Iannucci G, Minicucci L, Rodegher M, Sormani M P, Comi G, et al. (1999) Correlations between clinical and MRI involvement in multiple sclerosis: assessment using $T(1)$, $T(2)$ and MT histograms. J Neurol Sci 171: 121-129.
12. Lee H, Raiker S J, Venkatesh K, Geary R, Robak L A, et al. (2008) Synaptic function for the Nogo-66 receptor NgR1: regulation of dendritic spine morphology and activity-dependent synaptic strength. J Neurosci 28: 2753-2765.
13. Fu Q L, Liao X X, Li X, Chen D, Shi J, et al. (2011) Soluble Nogo-66 receptor prevents synaptic dysfunction and rescues retinal ganglion cell loss in chronic glaucoma. Invest Ophthalmol Vis Sci 52: 8374-8380.
14. Peng X, Zhou Z, Hu J, Fink D J, Mata M (2010) Soluble Nogo receptor down-regulates expression of neuronal Nogo-A to enhance axonal regeneration. J Biol Chem 285: 2783-2795.
15. Wang X, Duffy P, McGee A W, Hasan O, Gould G, et al. (2011) Recovery from chronic spinal cord contusion after Nogo receptor intervention. Ann Neurol 70: 805-821.
16. Jurewicz A, Matysiak M, Raine C S, Selmaj K (2007) Soluble Nogo-A, an inhibitor of axonal regeneration, as a biomarker for multiple sclerosis. Neurology 68: 283-287.
17. Steinman L (2009) The gray aspects of white matter disease in multiple sclerosis. Proc Natl Acad Sci USA 106: 8083-8084.
18. Derfuss T, Parikh K, Velhin S, Braun M, Mathey E, et al. (2009) Contactin-2/TAG-1-directed autoimmunity is identified in multiple sclerosis patients and mediates gray matter pathology in animals. Proc Natl Acad Sci USA 106: 8302-8307.
19. Tumani H, Lehmensiek V, Rau D, Guttmann I, Tauscher G, et al. (2009) CSF proteome analysis in clinically isolated syndrome (CIS): candidate markers for conversion to definite multiple sclerosis. Neurosci Lett 452: 214-217.
20. Comabella M, Fernandez M, Martin R, Rivera-Vallve S, Borras E, et al. (2010) Cerebrospinal fluid chitinase 3-like 1 levels are associated with conversion to multiple sclerosis. Brain 133: 1082-1093.
21. Kroksveen A C, Aasebo E, Vethe H, van P, V, Franciotta D, et al. (2012) Discovery and initial verification of differentially abundant proteins between multiple sclerosis patients and controls using iTRAQ and SID-SRM. J Proteomics
22. Dhaunchak A S, Becker C, Schulman H, De F O, Jr., Rajasekharan S, et al. (2012) Implication of perturbed axoglial apparatus in early pediatric multiple sclerosis. Ann Neurol 71: 601-613.
23. Xie F, Liu T, Qian W J, Petyuk V A, Smith R D (2011) Liquid chromatography-mass spectrometry-based quantitative proteomics. J Biol Chem 286: 25443-25449.
24. Hulst H E, Geurts J J (2011) Gray matter imaging in multiple sclerosis: what have we learned? BMC Neurol 11: 153.

25. Smith R D, Anderson G A, Lipton M S, Pasa-Tolic L, Shen Y, et al. (2002) An accurate mass tag strategy for quantitative and high-throughput proteome measurements. Proteomics 2: 513-523.
26. Wang Y, Yang F, Gritsenko M A, Wang Y, Clauss T, et al. (2011) Reversed-phase chromatography with multiple fraction concatenation strategy for proteome profiling of human MCF10A cells. Proteomics 11: 2019-2026.
27. Kelly R T, Page J S, Luo Q, Moore R J, Orton D J, et al. (2006) Chemically etched open tubular and monolithic emitters for nanoelectrospray ionization mass spectrometry. Anal Chem 78: 7796-7801.
28. Mayampurath A M, Jaitly N, Purvine S O, Monroe M E, Auberry K J, et al. (2008) DeconMSn: a software tool for accurate parent ion monoisotopic mass determination for tandem mass spectra. Bioinformatics 24: 1021-1023.
29. Elias J E, Gygi S P (2007) Target-decoy search strategy for increased confidence in large-scale protein identifications by mass spectrometry. Nat Methods 4: 207-214.
30. Peng J, Elias J E, Thoreen C C, Licklider L J, Gygi S P (2003) Evaluation of multidimensional chromatography coupled with tandem mass spectrometry (LC/LC-MS/MS) for large-scale protein analysis: the yeast proteome. J Proteome Res 2: 43-50.
31. Qian W J, Liu T, Monroe M E, Strittmatter E F, Jacobs J M, et al. (2005) Probability-based evaluation of peptide and protein identifications from tandem mass spectrometry and SEQUEST analysis: the human proteome. J Proteome Res 4: 53-62.
32. Monroe M E, Tolic N, Jaitly N, Shaw J L, Adkins J N, et al. (2007) VIPER: an advanced software package to support high-throughput LC-MS peptide identification. Bioinformatics 23: 2021-2023.
33. Zimmer J S, Monroe M E, Qian W J, Smith R D (2006) Advances in proteomics data analysis and display using an accurate mass and time tag approach. Mass Spectrom Rev 25: 450-482.
34. Stanley J R, Adkins J N, Slysz G W, Monroe M E, Purvine S O, et al. (2011) A statistical method for assessing peptide identification confidence in accurate mass and time tag proteomics. Anal Chem 83: 6135-6140.
35. Nesvizhskii M, Keller A, Kolker E, Aebersold R (2003) A statistical model for identifying proteins by tandem mass spectrometry. Anal Chem 75: 4646-4658.
36. Polpitiya A D, Qian W J, Jaitly N, Petyuk V A, Adkins J N, et al. (2008) DAnTE: a statistical tool for quantitative analysis of -omics data. Bioinformatics 24: 1556-1558.

What is claimed is:

1. A method for diagnosing and treating first-attack multiple sclerosis in a patient, the method comprising:
    a) isolating a cerebrospinal fluid (CSF) sample from the patient;
    b) contacting the CSF sample with reagents specific for each of a panel of biomarkers to assess expression of the biomarkers, wherein the panel of biomarkers comprises Neural epidermal growth factor like 2/cerebral protein-12, Cerebellin-1, Nogo receptor, Dickkopf-3 (RIG-like 7-1), Brevican, Chitinase-3-like 1 protein, and Neogenin; and
    c) comparing expression of each of the biomarkers in the CSF sample to expression of each of the biomarkers, respectively, in a control CSF sample to determine if expression of any of the biomarkers in the CSF sample is increased or decreased relative to biomarkers in the control CSF sample,
    wherein detection of increased expression of any of Neural epidermal growth factor like 2/cerebral protein-12, Cerebellin-1, Nogo receptor, or Dickkopf-3 (RIG-like 7-1) in the CSF sample relative to expression for each biomarker, respectively, in a control CSF sample is, for each biomarker, a positive indicator of first-attack multiple sclerosis in the patient; and detection of decreased expression of any of Brevican, Chitinase-3-like 1 protein, or Neogenin in the CSF sample relative to expression for each biomarker, respectively, in a control CSF sample is, for each biomarker, a positive indicator of first-attack multiple sclerosis in the patient, and
    identification of at least two positive indicators in the patient serves to diagnose the patient as a first-attack multiple sclerosis patient; and treating the patient diagnosed with first-attack multiple sclerosis by administering a therapeutically effective amount of a disease modifying agent for treating multiple sclerosis.

2. The method of claim 1, wherein the reagents specific for each of the panel of biomarkers comprise antibodies.

3. The method of claim 1, further comprising processing the CSF sample prior to step b.

4. The method of claim 3, wherein the processing comprises immunodepletion of abundant proteins and sample concentration and/or proteolytic enzymatic digestion.

5. The method of claim 1, wherein the at least two positive indicators correspond to increased or decreased expression of three, four, five, six, or seven of the biomarkers in the CSF sample relative to the control CSF sample.

6. The method of claim 1, wherein the at least two positive indicators comprise increased expression of Neural epidermal growth factor like 2/cerebral protein-12 and Cerebellin-1.

7. The method of claim 1, wherein the increase or decrease is at least about a fold change of 1.1.

8. The method of claim 1, wherein the patient has experienced one of the common initial symptoms of multiple sclerosis comprising a vision problem, weakness, imbalance, or sensory problems.

9. The method of claim 1, wherein the disease modifying agent for treating multiple sclerosis is Aubagio (teriflunomide), Avonex (interferon beta-1a), Betaseron (interferon beta-1b), Copaxone (glatiramer acetate), Extavia (interferon beta-1b), Gilenya (fingolimod), Novantrone (mitoxantrone), Rebif (interferon beta-1a), Tecfidera (dimethyl fumarate), or Tysabri (natalizumab).

10. A method for diagnosing and treating first-attack multiple sclerosis in a patient, the method comprising:
    a) isolating a cerebrospinal fluid (CSF) sample from the patient;
    b) contacting the CSF sample with reagents specific for each of a panel of biomarkers to assess expression of the biomarkers, wherein the panel of biomarkers comprises Neural epidermal growth factor like 2/cerebral protein-12, Cerebellin-1, Neural cell adhesion molecule 2, Neuronal cadherin, Nogo receptor, Kallikrein-6 (Neurosin), Ceruloplasmin, Dickkopf-3 (RIG-like 7-1), Activated leukocyte cell adhesion molecule (CD166), Clusterin (Apolipoprotein J, complement lysis inhibitor), Brevican, Chitinase-3-like 1 protein, Neogenin, Multifunctional protein MFP, collagen alpha 1 (XVIII) chain (Endostatin), Dystroglycan 1, Contactin 2, Ephrin type A receptor 4, Neural cell adhesion molecule L1 like protein, and Contactin 1 and comparing expression of each of the biomarkers in the CSF sample to expression of each of the biomarkers, respectively, in a control CSF sample to determine if expression of any of the biomarkers in the CSF sample is increased or decreased relative to biomarkers in the control CSF sample, wherein detection of increased expression of Neural epidermal growth factor like 2/cerebral protein-12, Cerebellin-1, Nogo receptor, or Dickkopf-3 (RIG-like 7-1) in the processed CSF sample relative to expression for each biomarker, respectively, in a processed control CSF sample is, for each biomarker, a positive indicator of first-attack multiple sclerosis in the patient;

and detection of decreased expression of Brevican, Chitinase-3-like 1 protein, or Neogenin in the processed CSF sample relative to expression for Neuronal cadherin in a processed control CSF sample is, for each biomarker, a positive indicator of first-attack multiple sclerosis in the patient, and identification of at least two positive indicators in the patient serves to diagnose the patient as a first-attack multiple sclerosis patient; and treating the patient diagnosed with first-attack multiple sclerosis by administering a therapeutically effective amount of a disease modifying agent for treating multiple sclerosis.

11. The method of claim 10, wherein the reagents specific for each of the panel of biomarkers comprise antibodies.

12. The method of claim 10, further comprising processing the CSF sample prior to step b.

13. The method of claim 10, wherein the at least two positive indicators correspond to increased or decreased expression of three, four, five, six, or seven of the biomarkers in the CSF sample relative to the control CSF sample.

14. The method of claim 10, wherein the at least two positive indicators comprise increased expression of Neural epidermal growth factor like 2/cerebral protein-12 and Cerebellin-1.

15. The method of claim 10, wherein the increase or decrease is at least about a fold change of 1.1.

16. The method of claim 10, wherein the disease modifying agent for treating multiple sclerosis is Aubagio (teriflunomide), Avonex (interferon beta-1a), Betaseron (interferon beta-1b), Copaxone (glatiramer acetate), Extavia (interferon beta-1b), Gilenya (fingolimod), Novantrone (mitoxantrone), Rebif (interferon beta-1a), Tecfidera (dimethyl fumarate), or Tysabri (natalizumab).

* * * * *